United States Patent [19]
Härle

[11] Patent Number: 4,892,516
[45] Date of Patent: Jan. 9, 1990

[54] SURGICAL AID

[75] Inventor: Anton Härle, Münster-Roxel, Fed. Rep. of Germany

[73] Assignee: Merck Patent Gesellschaft Mit Beschrankter Haftung, Darmstadt, Fed. Rep. of Germany

[21] Appl. No.: 598,546

[22] PCT Filed: May 29, 1983

[86] PCT No.: PCT/EP83/00092
§ 371 Date: Jan. 9, 1984
§ 102(e) Date: Jan. 9, 1984

[87] PCT Pub. No.: WO83/03967
PCT Pub. Date: Nov. 24, 1983

[30] Foreign Application Priority Data
May 7, 1982 [DE] Fed. Rep. of Germany ....... 3217109

[51] Int. Cl.$^4$ .............................................. A61B 17/18
[52] U.S. Cl. ........................................ 604/57; 604/93; 604/288; 424/426

[58] Field of Search .................. 604/891, 304, 57, 93, 604/20, 21, 368; 128/288, 92 G, 1.2; 3/1; 424/426

[56] References Cited

U.S. PATENT DOCUMENTS

| 3,882,858 | 5/1975 | Klemm | 128/92 G |
| 4,066,083 | 1/1978 | Ries | 128/334 R |
| 4,186,448 | 2/1980 | Brekke | 604/891 |
| 4,329,185 | 5/1982 | Dimer et al. | 3/1 |
| 4,510,924 | 4/1985 | Gray | 128/1.2 |

FOREIGN PATENT DOCUMENTS

| 0011528 | 5/1980 | European Pat. Off. | 128/92 G |
| 0581935 | 11/1977 | U.S.S.R. | 128/92 G |

Primary Examiner—C. Fred Rosenbaum
Attorney, Agent, or Firm—Millen, White & Zelano

[57] ABSTRACT

The invention proposes a surgical aid which contains pharmaceutical active compounds in support materials which permit protracted release of the active compounds, this aid being designed in the form of a flat article provided with free spaces, and, as a rule, the individual free spaces having, at least predominantly, an area of at least 0.1 cm$^2$.

10 Claims, 2 Drawing Sheets

SURGICAL AID

BACKGROUND OF THE INVENTION

1. Field of the Invention

The invention relates to a surgical aid which contains pharmaceutical active compounds in support materials which permit protracted release of the active compounds.

2. Technical Considerations and Prior Art

Agents which contain antibiotics and are used as surgical materials for controlling infections have been disclosed in German Patent Specification No. 2,320,373. They are used for, for example, in filling osteomyelitic cavities and are used in the form of beads which are connected together by means of threads or wires. These beads, which are produced from a material which is not absorbable by the body, must subsequently be surgically removed from the wound and thus cannot be advantageously used for managing infections of soft tissues. In addition, it is only possible with great difficulty to chieve uniform distribution of the beads over a relatively large wound area.

The use of partially absorbable multicomponent compositions which are based on physiologically tolerated substances and contain medicaments and which are intended to serve as a permanent replacement for bone and, with this object, are completely integrated into the biological system, without there being the necessity for later reoperation to remove the implant, are known from German Specification No. 2,917,037. This composition, which takes the form of granules or a moulded composition, cannot be used for managing normal wounds since integration into the bone is impossible in this instance.

SUMMARY OF THE INVENTION

Thus, an object of this invention was to find a surgical aid which is suitable for absorbing and releasing, in a protracted manner, medical active compounds and which, in particular, can also be used for normal wounds.

Another object was to design the agent such that uniting the tissue in the surfaces of the wound can take place as far as possible uninhindered, without the surgical aid which is used interfering with this reuniting or there being a necessity for its later removal.

Finally, still another object was to design the agent such that it permits medical active compounds to be placed so as to act at sites which can be accurately determined beforehand, for example in a uniform distribution over the entire wound area, or specifically localised at one or more points.

This object has been achieved by the present invention.

Thus the invention relates to a surgical aid, which contains pharmaceutical active compounds in support materials which permit protracted release of the active compounds, and which is characterised in that it is designed in the form of a flat article provided with free spaces, as a rule the individual free spaces having, at least predominantly, an area of at least 0.1 cm$^2$.

A significant advantage of the aids according to the invention is that medical active compounds can be introduced into the body at defined spacings from one another and thus in an exactly defined spatial distribution, and can display their actions at sites in the body which can be accurately determined beforehand. Direct contact with the surfaces of the wound, and thus healing without difficulty and without the formation of scar tissue, is made possible by the flat design of the aid and the high proportion of free spaces. The aids can be designed in the form of, for example, lattices or perforated plates which have free spaces which are sufficiently large for the tissue in the surfaces of the wound to unite.

DESCRIPTIONS OF THE PREFERRED EMBODIMENTS

Figure 1:
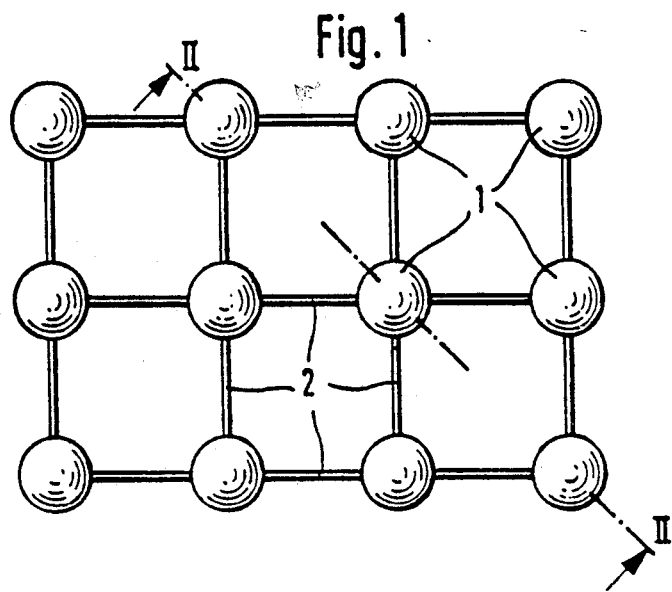
FIG. 1 is a top planar view a first embodiment of the surgical aid of the instant invention, wherein the surgical aid is configured as a lattice with medicated beads disposed at points of intersection of the threads comprising the lattice.
Figure 2:
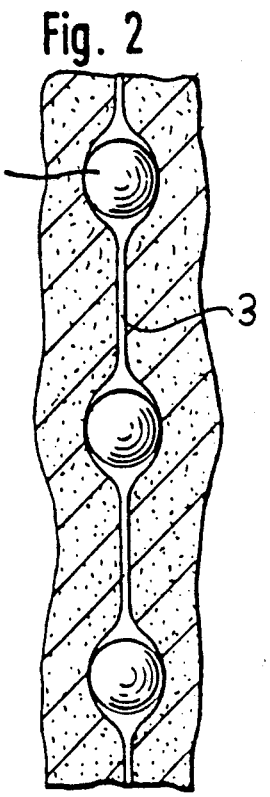
FIG. 2 is a side view, in section, showing the lattice of FIG. 1 implanted in a wound, wherein the lattice itself is shown in section taken along line II—II of FIG. 1.

Some preferred embodiments of the invention are shown in the drawings. FIG. 1 shows a plan view of a flat article made of absorbable threads (2) which form a lattice, the active compounds which become medicinally effective being located at the points of intersection (1) of the lattice. FIG. 2 shows a cross-section along the line II—II through a lattice of FIG. 1 which has been inserted into a wound.

In this embodiment, the threads (2) which form the lattice are designed to be relatively thin, and the significant mass is localised at the points of intersection. This has the advantage that the surfaces of the wound (3) can come into direct contact over significant areas of the wound. The active compounds are essentially localised at the points of intersection (1) from where diffusion into the surrounding free spaces takes place. However, it is obvious that the threads (2) can also contain active compounds.

Figure 3:
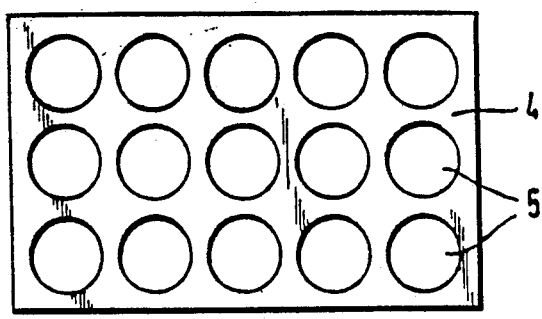
FIG. 3 is a top view of another embodiment of the instant invention wherein the surgical aid is configured as a perforated plate.

FIG. 3 shows a flat article which is designed as a plate (4) containing free spaces (5). It is possible and preferable for this plate to be composed entirely of an absorbable material which contains the active compounds to be released. However, it is also possible in principle for some of the free spaces (5) to be charged with moulded items containing active compound, while the free spaces (5) which remain empty permit the tissue in the two layers of the wound which are separated from one another to unite. In this instance, it is possible to use, for example, the beads known from German Patent Specification No. 2,320,373, and these can, where appropriate, be connected together by wires or threads so that, after absorption of the plate (4), the beads can be withdrawn in a manner known per se. However, due to the arrangement of the beads in the plate, uniform distribution of the active compounds in the area of the wound is made possible on the one hand, and entanglement of the beads on withdrawal is prevented on the other hand.

Figure 4:
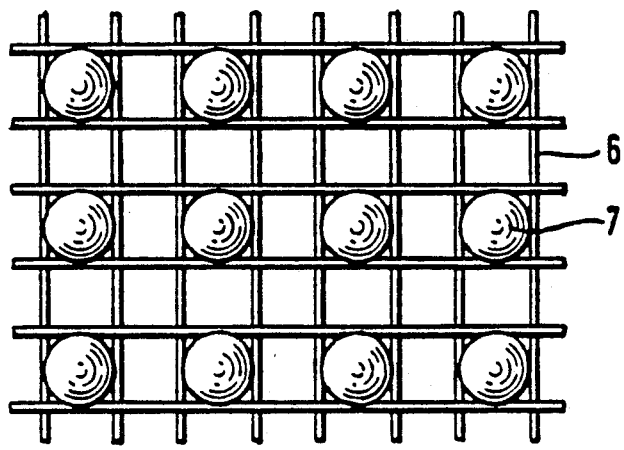
FIG. 4 is a top view of a third embodiment of the invention, wherein a lattice is provided with medicated beads disposed in the spaces defined by the lattice.

FIG. 4 shows a flat article which is again designed as a lattice (6). It is possible for this lattice to be used for immobilising moulded items containing active compounds, and these are designed as beads (7) in this instance. However, as an alternative or supplement to this, it is also possible for the lattice itself to be composed of material containing active compound. In this instance, it is also possible, inter alia, to charge the lattice (6) and the moulded items (7) with different active compounds. Due to the greater mobility of the lattice (6) compared with the plate (4), it is possible to immobilise the moulded items (7) containing active compounds in any desired spatial distribution, for example even around a bone or stump of bone.

As a rule, the aids according to the invention are manufactured from an absorbable material which is tolerated by the body. Large numbers of such materials are known and have already been proposed for other surgical purposes. In this context, the following are merely mentioned as examples: polyglycolides, polylactides, polyhydroxycarboxylic acids, polyamino acids and collagen. However, in certain cases it can also be necessary to use non-absorbable materials. This is the case, for example, when the active compounds contained in the flat articles are not degraded in the body but, like, for example, radioisotopes, must be removed again from the body after a certain duration of action. A lattice which is not dissolved can be removed again from the body relatively easily, but good spatial distribution of the active compounds is ensured during the time it is present in the body.

Figure 5:
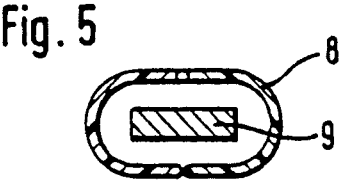
FIG. 5 is a side view, in section, of a fourth embodiment of the invention showing a capsule having a radioisotope introduced therein, which capsule is surrounded by a shell and which capsule may be used with the lattice configuration of FIGS. 1 and 4 or the plate configuration of FIG. 3.

When using radioisotopes, for example, it can also be advantageous to use the moulded item shown in FIG. 5, which comprises a capsule (8) into which a radioisotope (9) can be introduced. The capsule (8) is manufactured from a non-absorbable material, such as, for example, an acrylate polymer, in the form of half-shells which, after introducing the emitter, can be bonded or sealed together so as to form a shell which surrounds the radioactive isotope 9. This type of capsule (8) can be held in the body by an absorbable lattice in accordance with FIG. 1 or 4 or an absorbable plate in accordance with FIG. 3. It is ensured, by becoming embedded in the wound and by the absorption of the lattice, that the capsule is located at the desired site and remains there so that the exposure to radiation can be accurately controlled, and desired localised irradiation can be achieved without there being a need to fear that the capsule can be displaced when the patient moves. As soon as the areas of the wound have grown together through the lattice or the plate, displacement of the capsule (8) is no longer possible. In this instance, the active compounds, for example antibacterials, contained in the lattice or plate ensure that healing of the areas of the wound takes place without difficulty.

The term "active compound" is employed in a very wide sense and comprises all items for parenteral use which are intended for curing, alleviating, treating and/or preventing illnesses in humans and animals, or are able to influence a bodily function of humans or animals.

Antibacterial active compounds of a variety of types, in particular antibiotics, should be particularly mentioned. Their spectrum of action should comprise Gram-positive or Gram-negative pathogens or, preferably, both groups. Where, possible, the induction of resistance in the pathogens by the active compounds should be only slow or zero. Of the antibacterial active compounds, the following antibiotics may be picked out as examples;

aminoglycoside antibiotics, such as amikacin, butirosin, dideoxykanamycin B (DKB), fortimycin, gentamycin, kanamycin, lividomycin, neomycin, netilmicin, ribostamycin, sagamycins, seldomycins and their epimers, sisomicin, sorbistin, tobramycin, streptomycins; lincoycins, such as clindamycin and lincomycin, and rifamycins, such as rifampicin and rifamycin.

The aminoglycoside antibiotics, especially gentamycin, are particularly suitable for this purpose because of their broad spectrum of antibacterial action.

It is also possible to combine together two or more of these antibiotics, for example gentamycin with clindamycin; in addition, combinations of these antibiotics with other active compounds, for example with antiseptics, are suitable.

Other active compounds are also preferred, for example antiseptics (such as bromochlorophene, hexetidine, buclosamide, salicylic acid, cerium nitrate, chlorhexidine, 5-chloro-8-hydroxyquinoline, copper 8-hydroxyquinolate, acridine orange, undecenoic acid, undecoylium chloride, silver salts, such as silver sulfadiazine, mafenide, nitrofurazone, cloflucarban, tribromsalan, taurolin and noxythiolin), tuberculostatics, such as, for example, streptomycin, rifamycins and isonicotinoyl hydrazide, also antiinflammatories (such as salicylates, phenylbutazones, indometacin, ibuprofen, p-aminophenol derivatives [for example acetaminophene], pyrazolones and hydrocortisone palmitate) and cytostatics (such as methotrexate, fluorouracil, vinblastin, doxorubicin and prednisone). Where appropriate, it is also possible to combine together active compounds directed at different indications.

It is also possible to adjust the mode of release of the active compounds to suit requirements. Thus, on the one hand, it is possible to control the rate of release by the selection of the support material and the concentration of the active compound in the support material. On the other hand, it is also possible specifically to reduce the solubility of the active compound and thus to achieve greater retardation. For this purpose, especially for antibiotics, but also for other groups of active compounds, the formation of sparingly soluble salts can be carried out in many cases. For example, it is particularly suitable for aminoglycoside antibiotics to form salts with phosphoric esters of hydroxyflavanoids.

The amount of active compounds to be added can be varied within wide limits and essentially depends on its activity. In general, the amount of the active compound is between about 0.2 and 20% by weight, preferably about 5-15% by weight, relative to the surgical aid. However, in individual cases, it is necessary to aim at the tissue concentrations which are necessary to influece the illness effectively.

The surgical aid according to the invention provides immobilisation for medically effective active compounds directly at the site where there is a therapeutic necessity for this. At the same time, it makes it possible for the surgeon to select, depending on the use for a particular case, the desired dose which is already determined during production of the flat article. It is essential that the free spaces present in the flat article are sufficiently large to permit the tissue of the wounds to unite.

Thus, the proportion of these free spaces in the total area is preferably at least 60% and, where appropriate, even 75% or above. Moreover, each individual free space should have an area of at least about 0.1 cm$^2$, preferably at least about 0.25 cm$^2$. However, it is also possible to produce free spaces of a size ranging up to several square centimeters, and this is very advantageous, particularly in respect of the direct uniting of the surfaces of the wound.

Thus, the invention makes available a new and very advantageous surgical aid.

I claim:

1. A surgical aid, capable of being incorporated into soft tissue wounds, the surgical aid comprising a pharmaceutically active compound retained in a support structure, the surgical aid permitting protracted release of the active compund, the support structure being configured as a flat article provided with individual free spaces, each individual free space having an area of at least 0.1 cm$^2$, the total area of the free spaces comprising at least 60 percent of the area of the flat article.

2. The surgical aid according to claim 1, wherein the support structure is made from material which is adsorbable by the body.

3. The surgical aid according to claim 2, wherein molded items containing the active compound are located in defined spacings at areas which contain no active compound.

4. The surgical aid according to claim 3, wherein the molded items are capsules constructed of half-shells.

5. The surgical aid according to claim 1, wherein the support structure is a lattice formed of threads crossing at points of intersection, the active compound being concentrated at the points of intersection of the lattice.

6. The surgical aid according to claim 5, wherein molded items containing the active compound are located with defined spacings at the intersections.

7. The surgical aid according to claim 6, wherein the molded items are capsules constructed of half-shells.

8. The surgical aid of claim 5, wherein the active compound is also disposed on the threads.

9. The surgical aid according to claim 1, wherein the flat article is in the form of a lattice having threads crossing at points of intersection to define spaces between the threads, and wherein molded items containing the active compound are disposed in some of the spaces, the remaining spaces being said free spaces.

10. A surgical aid capable of being incorporated into soft tissue, the surgical aid containing radioactive isotopes retained in support structure, the surgical aid permitting protracted application of radiation from said radioactive isotopes, the surgical aid comprising a flat support structure having free spaces, each individual free space having an area of at least 0.1 cm$^2$, wherein the total area of the free spaces comprise at least 60 percent of the area of the flat support structure, a plurality of molded shells distributed in spaced relation in the flat support structure, the radioactive isotopes being retained in the molded shells and being completely surrounded thereby.

* * * * *